United States Patent [19]

Arakawa et al.

[11] Patent Number: 4,601,284

[45] Date of Patent: Jul. 22, 1986

[54] ENDOSCOPE CONNECTING SYSTEM

[75] Inventors: Satoshi Arakawa, Oomiya, Japan; David H. Cooper, Saratoga, Calif.

[73] Assignee: Fuji Photo Optical Co., Ltd., Japan

[21] Appl. No.: 730,947

[22] Filed: May 6, 1985

[30] Foreign Application Priority Data

May 18, 1984 [JP] Japan .................... 59-100287

[51] Int. Cl.⁴ .................... A61B 1/04
[52] U.S. Cl. .................... 128/6; 358/98
[58] Field of Search .................... 128/4, 6; 358/98

[56] References Cited

U.S. PATENT DOCUMENTS

| | | | |
|---|---|---|---|
| Re. 31,289 | 6/1983 | Moore et al. | 128/6 |
| Re. 31,290 | 6/1983 | Moore et al. | 128/6 |
| 4,146,019 | 3/1979 | Bass et al. | 128/6 |
| 4,253,447 | 3/1981 | Moore et al. | 128/6 |
| 4,253,448 | 3/1981 | Terada | 128/4 |
| 4,261,344 | 4/1981 | Moore et al. | 128/6 |
| 4,414,608 | 11/1983 | Furihata | 128/6 X |
| 4,475,539 | 10/1984 | Konomura | 128/6 |
| 4,539,586 | 9/1985 | Danna et al. | 128/6 X |

*Primary Examiner*—William H. Grieb
*Attorney, Agent, or Firm*—Parkhurst & Oliff

[57] ABSTRACT

An endoscope connecting system having as its imaging system a solid state imaging device for generating a video signal containing image information of an interested object which is transmitted to a display to be visualized such as a television picture comprises a fiberoptic endoscope having an eyepiece section on its control section, a video endoscope having a solid state imaging device disposed in its insertion section for generating a video signal, an adaptor having a solid state imaging device therein which is detachably mounted on the eyepiece section of the fiberoptic endoscope and a light source device for producing illumination light to enter the fiberoptic endoscope or the video endoscope in a red, green and blue sequence. The adaptor permits the connection of the fiberoptic endoscope to video signal processing means for the video endoscope so as to display an image of the interested object on the monitor equipment.

4 Claims, 8 Drawing Figures

ENDOSCOPE CONNECTING SYSTEM

BACKGROUND OF THE INVENTION

1. Field of the Invention

The present inventioin relates to an endoscope connecting system, and more particularly relates to an endoscope connecting system for presenting an image of an object of interest on the screen of a viewing equipment corresponding to a video signal provided by an endoscope of the type having in its imaging system a solid state imaging device.

2. Description of the Prior Art

In order to observe or inspect the inside of a cavity or opening of a living body or machinary, a fiberoptic endoscope is generally used. As well known in the art, a fiberoptic endoscope includes an image transmission optical fiber bundle, an objective lens for forming an image of an object of interest on one end face of the image transmission optical fiber bundle and an eyepiece lens for providing an enlargement of the image appearing on the opposite end face of the image transmission optical fiber bundle. Specifically, as shown in FIG. 1, the fiberoptic endoscope comprises a control section 10, a flexible, insertion section 12 connected to the control section 10, which section being insertable into a cavity of a living body to be observed or inspected, and a connector section 16 for connecting the endoscope to a control unit 14 incorporating an illumination light source, control devices, etc. therein.

In such fiberoptic endoscopes as having an image transmission optical fiber bundle for transmitting an optical image of an object from one end to the opposite end thereof, the control section 10, as shown in FIG. 2, comprises a grip section 15 which is necessarily grasped by one hand and an eyepiece section 17 disposed on the uppermost end of the control section 10.

When using the conventional fiberoptic endoscope shown in FIGS. 1 and 2 for observation, an operator is required to bring the control section 10 close to his face by raising his arm, otherwise to bring his head close to the eyepiece section 17 by bending his body foward. Therefore, the operator will be obliged to assume an unnatural posture, resulting in that his arm, waist and the like become numb. There is nothing like having no such numb sensation.

Recently, on the other hand, there has been proposed video endoscopes of the type having in its imaging system a solid state imaging device, such as a charge coupled device (CCD) or a metal oxide silicon (MOS) image sensor, which is carried in a viewing head thereof adapted for insertion into the cavity of an object to be observed. The solid state imaging device accepts visual image information of a scene contained in the object and converts it to an electrical output data signal or a video signal for presenting a picture of the scene on the screen of an viewing equipment such as a monitor television receiver.

Because such video endoscope employing a solid state imaging device, different from a conventional fiberoptic endoscope which is adapted to form an optical image on one end face of an image transmission fiber bundle for observation or inspection, is adapted to presents a visual image on a monitor screen, it has the advantage of the preparation of no eyepiece section and of easy handling in an easy posture.

A conventional fiberoptic endoscope having in its imaging system an image transmission optical fiber bundle will be easily handled in an easy posture just as the video endoscope mentioned above if the fiberoptic endoscope is adapted to presenting a visual image on a viewing screen. In order to satisfy the condition, it is required for the fiber optic endoscope to be equipped with a means for converting a visual image information into a video signal and to be used with a control unit including an illumination light source and a video signal processor which have their functions exactly same as that of a control unit for the video endoscope. If functions of these control units are different from each other, it is undesirable in prompt operation and economical efficiency. It has, therefore, been expected for the economical efficiency to prepare a control unit commonly used with both the fiberoptic endoscope and the video endoscope.

SUMMARY OF THE INVENTION

An object of the present invention, accordingly, is to provide an endoscope connecting system which can make it possible that presenting an image of an object to be observed on a viewing equipment is effected by connecting a fiberoptic endoscope of the type having in its imaging system an image transmission optical fiber bundle to a control unit which is adapted to be in cooperation with a video endoscope of the type having in its imaging system a solid state imaging device so as to present an image of an object to be observed on the viewing equipment.

To achieve the above-mentioned object, according to the present invention, there is provided a connecting system for endoscopes which comprises a first endoscope of the type having an insertion section to be inserted into a cavity of an object of interest, a control section coupling the end of the insertion section and an imaging system comprising first optical means for illuminating the inside of the cavity and optical image transmission means for forming and transmitting an image of the object to be observed through an eyepiece section mounted on the control section, the illumination means and image transmission means being incorporated within the first insertion section, a second endoscope of the type having a second insertion section to be inserted into a cavity of an object of interest on an imaging system comprising second optical means incorporated within the second insertion section for illuminating the inside of the cavity and a first solid state imaging device incorporated in the forward end of the second insertion section for accepting visual image information of a scene of the object and converting it into a video signal so as to present an image of the object on a viewing equipment, adaptor means having therein a second solid state imaging device and being adapted to be detachably connected to the eyepiece section of the first endoscope, and a control unit including a video signal processor for processing the video signal from the first solid state imaging device and an illumination light source device for producing illumination light directed to the first and second optical illumination means in a red, green and blue sequence. The first endoscope with the adaptor means connected thereto is capable of functioning as a video endoscope in such a way that the second solid state imaging device accepts visual image information through the eyepiece section and converts it into a video signal which is directed through the video signal processor to the viewing equipment to present an image of an object thereon.

According to the feature of the present invention, the endoscope connecting system makes it possible to connect both types of endoscopes to the control unit which is primarily designed to be used together with endoscopes of the type having a solid state imaging device. The compatibility of the control unit results in a high economical efficiency and convenience.

BRIEF DESCRIPTION OF THE DRAWINGS

The exact nature of this invention, as well as other objects and advantages thereof, will be readily understood from consideration of the following specification relating to the accompanying drawings, in which like reference characters designate the same or similiar parts through out the figures thereof and wherein.

DETAILED DESCRIPTION OF THE INVENTION

Description will hereunder be given of the preferred embodiments of a video endoscope system according to the present invention with reference to the accompanying drawings.

Figure 3:
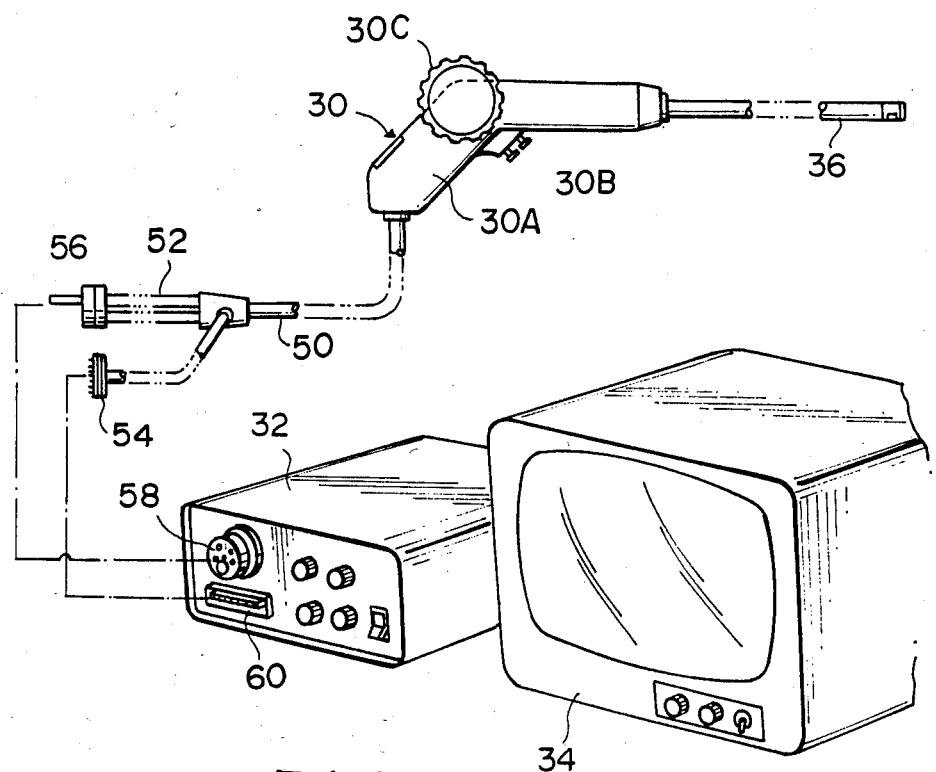
FIG. 3 is a general schematic view of a video endoscope system.
Figure 4:
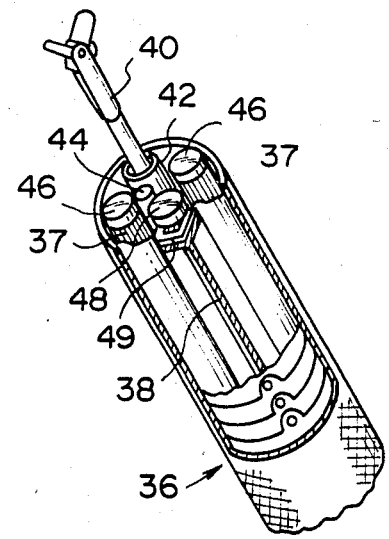
FIG. 4 is a schematic perspective view showing an internal arrangement of the viewing head of the video endoscope of FIG. 3.

Refering now in particular to FIG. 3, shown therein is a video endoscope system comprising a video endoscope of the type having in its imaging system an image pick-up device arranged in its viewing head, a control unit 32 including therein a light source and various control means and a monitor television receiver 34. The video endoscope well known in itself has a control section 30 comprising a pistol grip 30A, control buttons 30B for suction and air and water supply and a control knob 30C for bending of an insertion section 36 insertable into a cavity of an object of interest such as a cavity of a living body. The insertion section 36 has, as shown in FIG. 4, an internal arrangement in its viewing head including illumination light transmission means 37, 37 of optical fiber bundle, video signal transmission cables 38, a guide tube 42 for suction and/or a forceps 40, a tube 44 for air and water supply and the like. The viewing head is controllably bent in desirable directions by manipulation of the control knob 30C. The light entrance face of each illumination light transmission means 37 of optical fiber bundle is placed about within a plane to which light rays from a light source described hereunder are condensed and, on the other hand, the light emitting face is placed within the focal plane of a diffusion lens 46. A solid state imaging device 49 coupled to the video signal transmission cables 38 is placed within the focal plane of an objective lens 48. The solid state imaging device 49 and the objective lens 48 may be placed perpendicular to the axis of the insertion section 36. Connected to the end portion of the pistol grip 30A of the control section 30 is a connector section 50 which has the proximal end bifurcated with one arm being coupled to a connector 54 and the other to a plug 52. The plug 52, which is identical with that of a conventional fiberoptic endoscope in structure, includes therein a light guide rod 56, terminal pins for electrically connecting the control bottons 30B to control means for air and water supply bulbs, a tube to be connected to an air supply pump located within the control unit 32 and the like. The plug 52 is so structured as to be connected to and disconnected from a socket 58 on the control unit 32 with one touch. The connector 54 is connected to a socket 60 on the control unit 32 to permit the application of driving signal from the control unit 32 to the solid state imaging device 49 and the transmission of video signal from the solid state imaging device 49 to the control unit 32.

Figure 5:
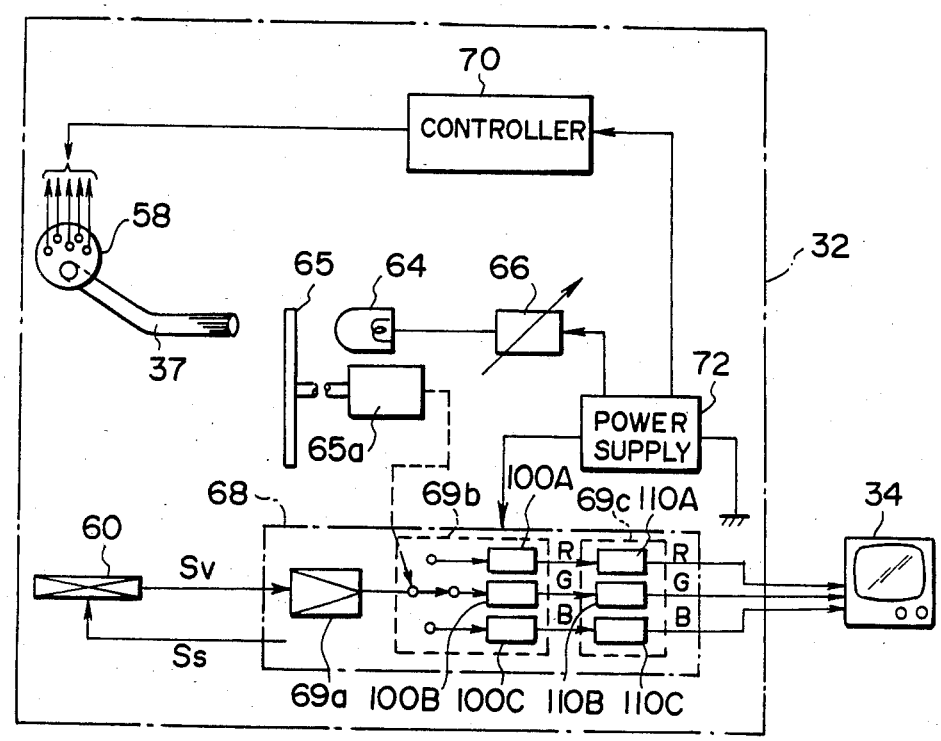
FIG. 5 is a block diagram showing a control for the video endoscope system of FIG. 3.

Refering to FIG. 5, shown therein in a block diagram form, is the control unit 32 which includes therein a manually operable regulator 66 for the intensity of light from the light source 64, a rotatable color filtering disc 65 driven by a motor 65a which carries color filters of red(R), green (G) and blue(B) annularly arranged every angle of either 120°/n (n is integral) for transmitting only light relating to one selected primary color in sequence while blocking all other, a processing means 68 for supplying driving signal Ss to the solid state imaging device 49 and for seperating a video signal Sv from the solid state imaging device 49 into dot sequential signals of three primary colors in synchronism with the alternation of the filters, a controller 70 for controlling the valbes in cooperation with the operation of the control buttons 30 and a power supply 72 for the processing means 68. The processing means 68 comprises an amplifier 69a for amplifying the video signal Sv, a signal separation part 69b comprising band-pass filters 100A, 100B and 100C for separating the amplified video signal into three primary color video signals and an amplification part 69c comprising three amplifiers 110A, 110B and 110C for the respective separated video color signals. Although, in this embodiment, three primary color filters are employed to produce three primary color lights, it may be allowed to use three lamps for emitting red, green and blue light, respectively.

The operation of the video endoscope mentioned above is as follows. An operator connects at first the plug 52 to the socket 58 of the control unit 32 and then the connector 54 to the socket 60 of the same. After turning on power supply switches for the control unit 32 and the monitor television receiver 34, the light intensity regulator 66 is adjusted by the manual operation of a knob (not shown) provided on the front panel of the control unit 32 so as to emit a desired intensity of light from each lens 46 disposed in front of the illumination light transmission optical fiber bundle 37. Thereafter, the operator grasps the pistol grip 30a and inserts gradually the insertion section 36 into a cavity to be observed, while watching an image of the inside of the cavity on the screen of the monitor lelevision receiver 34. When the viewing head of the insertion section 36 is located in vicinity of an interested region of the inside of the cavity, the operator manipulates the control knob 30C to adjust slightly and fix the viewing head of the insertion section 36 so as to present an aimed image of the viewing region on the screen of the monitor television receiver 34. According to requirements, the control button 30B is pushed with the forefinger for air and water supply or suction, and a forceps 40 or other surgical instrument is introduced through an entrance (not shown) formed in the control section 30 into the cavity for the purpose of picking a piece of flesh or mucous membrane of a diseased part.

Figure 1:
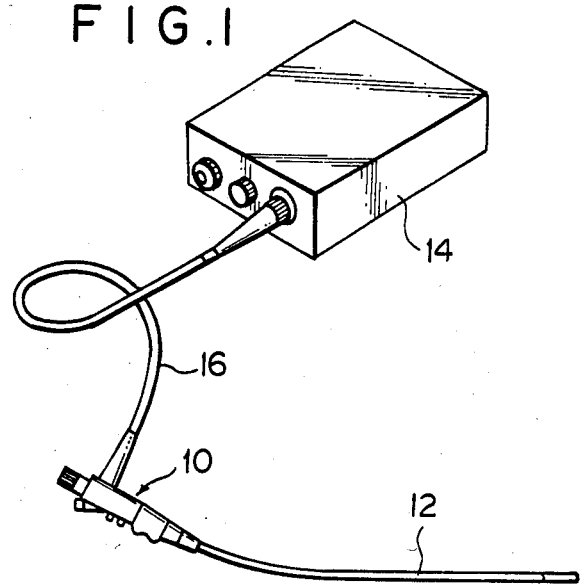
FIG. 1 is a general schematic view of a conventional fiberoptic endoscope system.
Figure 2:
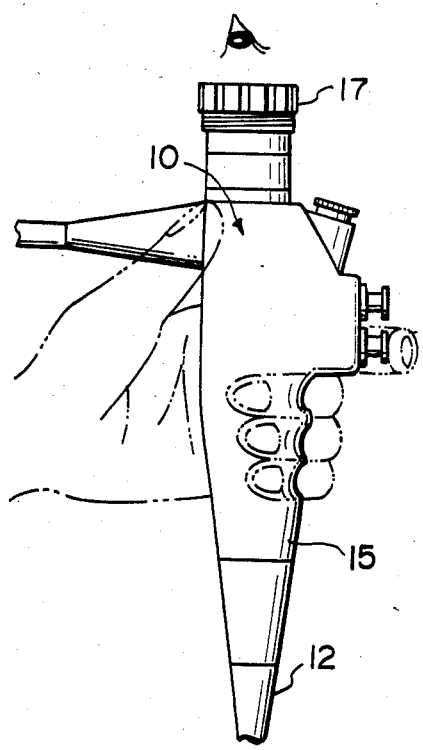
FIG. 2 is an elevational view of a control section of the conventional fiberoptic endoscope of FIG. 1.
Figure 6:
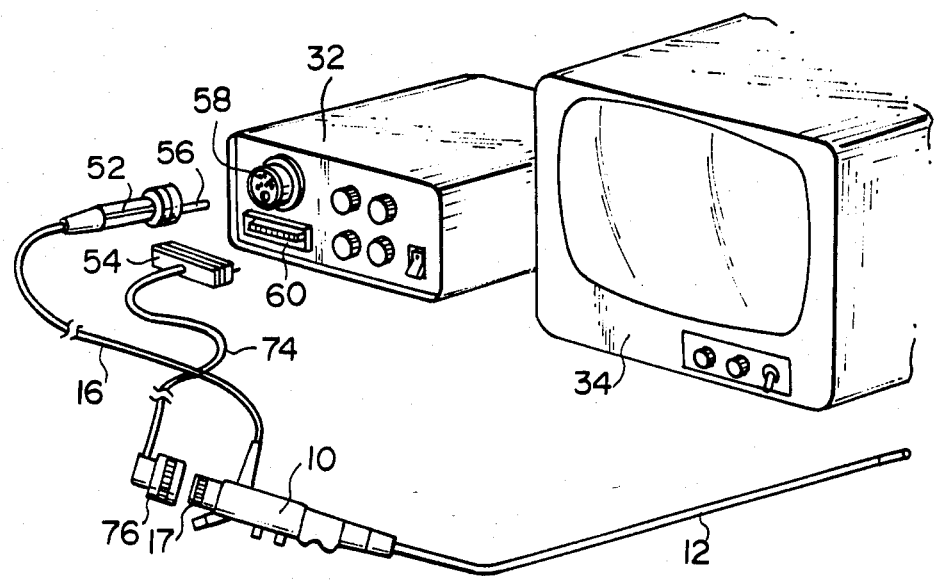
FIG. 6 is a general schematic view of an embodiment of the endoscope connecting system according to the present invention.

Refering next to FIG. 6, there is shown an embodiment of the endoscope connecting system of the present invention in which a conventional fiberoptic endoscope is used to present an image of a viewing region on the screen of the monitor television receiver 34. In this embodiment, the fiber optic endoscope with its control section 10, insertion section 12, connection section 16 and eyepiece section 17 are exactly the same as that shown in FIG. 1. For presenting an image on the screen of the monitor television receiver 34 by using the control unit 32 which is used with the video endoscope described above, there is provided in this system an adaptor 74. On the other hand, the opposite end of the adaptor 74 is provided with a connector 54 having the same specification as the connector 54 shown in FIG. 3 and being connectable to the socket 60 of the control unit 32. The connector section 16 at its one end has a plug 52 identical with the plug shown in FIG. 3 which is connectable to the socket 58 of the control unit 32. When the conventional fiberoptic endoscope is connected to the control unit 32 for video endoscopes, illumination light emitted from the light source 64 within the control unit 32 is transmitted through the light guide rod 56 and the illumination light transmission means 37 of optical fiber bundle extending through the connector section 16, control section 10 and the insertion section 12 to its viewing head for illuminating an interested viewing region inside a cavity. The connection of the connector 54 of the adaptor 74 permits to apply driving signals to the solid state imaging device in the connector 76 and to transmit a video signal generatd by the solid state imaging device to the control unit 32. The video signal is processed by the processing means 68 in the control unit 32 so as to present an image on the screen of the monitor television receiver 34.

Figure 7:
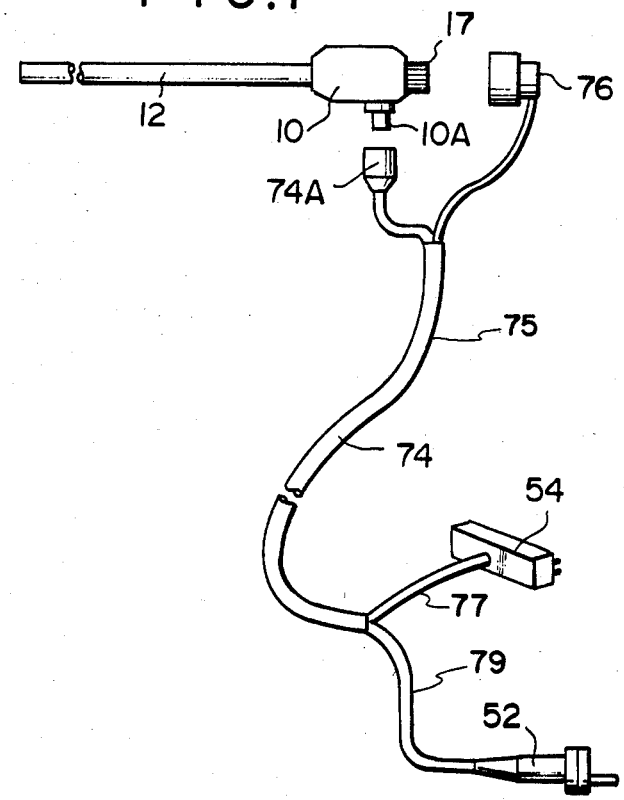
FIG. 7 is a schematic view of an embodiment of a video endoscope according to the present invention.

Refering now to FIG. 7, shown therein is a conventional fiberoptic endoscope different from the fiberoptic endoscope shown in FIG. 6. In this drawing, parts identical with or similar to that of the fiberoptic endoscope of FIG. 6 are designated by like reference numerals for the abbreviation of description. Although the adaptor 74 is provided as a special cable for the imaging device separately from the fiberoptic endoscope, an adaptor 75 of the embodiment shown in FIG. 7 includes an imaging device cable 77 and a junction light transmission fiber bundle 79 incorporated with each other. The one proximal end of the adaptor 75 is bifurcated with each arm being coupled to a connector. The connector 76 of one arm includes a solid state imaging device incorporated therewith. Another connector 74A is adapted to optically couple the end of the light transmission fiber bundle to the end 10A of the light transmission fiber bundle fixed in a part of the control section 10. The plug 52 and the connector 54 are adapted to be connected to the sockets 58, 60 on the control unit 32 in exactly the same way as described in FIG. 6. As described above, the adaptor 75 permits the fiberoptic endoscope to be connected to the control unit 32 for the video endoscope so as to present an image of a viewing region of a diseased part on the screen of the monitor television receiver 34.

As described above, according to the endoscope connecting system of the present invention, the fiberoptic endoscope having an eyepiece section is connected to the control unit for the video endoscope having in its imaging system a solid state imaging device disposed in its viewing head by connecting the adapter adapted to be mounted on the eyepiece section. The provision of the adapter makes the control unit commonly available for the both type of endoscopes, resulting in an economical use of endoscope system.

Figure 8:
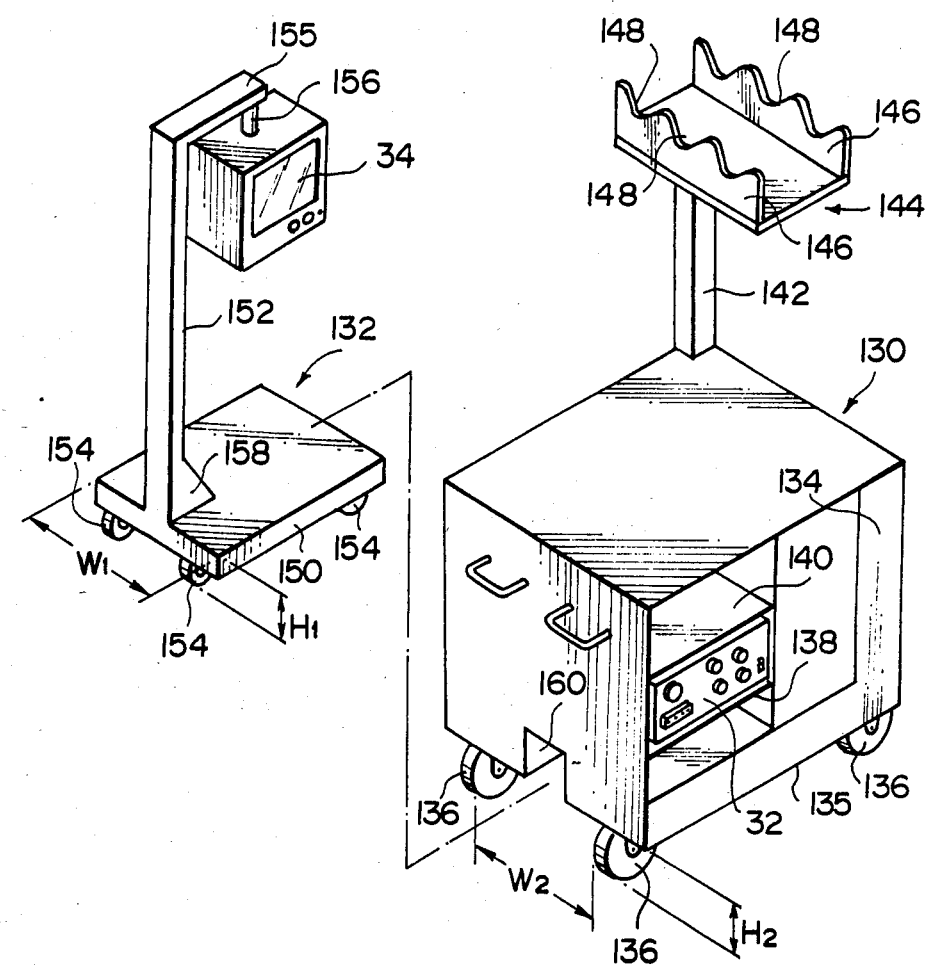
FIG. 8 is a perspective view of a frame for supporting the video endoscope system.

FIG. 8 shows a supporting frame for the endoscope system of the present invention which comprises a cart 130 capable of accommodating therein the control unit 32 including a light source, a power supply, a video signal processing device and other devices required for image processing and a stand 132 for suspending the monitoring television set 34 therefrom. The cart 130 has a housing 134 as a main portion thereof with four casters 136 mounted under its bottom panel for easy and unrestricted carriage. The housing 134 is divided into several compartments with partition plates 138, 140 for accommodating the control unit 32 and other video signal processing devices such as a video tape recorder in the respective compartments. A post 142 set up on the housing 134 is provided on its top end a holder 144 for supporting endoscopes with their control sections put thereon. The holder 144 comprises side plates 146 with corrugated edges 148 which are disposed opposite to each other. The stand 132 comprises a base 150 with four casters 154 mounted under its bottom and a post 152 having an inverted L-shape. From the laterally extending arm of the post 152 the monitoring television set 34 is rotatably suspended with a supporting pivot 156. The base 150 of the stand 132 has its width W1 more narrow than the width W2 of the cart 130 so as to enable the base 150 to get into a space left under the bottom of the cart 130. The cart 130 is formed with a groove 160 which allows a reinforcing member 158 attached to te base of the post 152 to get thereinto.

The supporting frame described above makes it easy to operate an endoscope as watching an image of viewing region presented on the screen of the monitoring television set 34 suspended from the stand 132. In practice, the stand 132 will be moved to a desired place in an operating room which is relatively small so as to give an operator an unrestricted vision.

In should be apparent to those skilled in the art that above-described embodiment represents but one of the many possible specific embodiments of the present invention. Numerous and varied other embodiments can be devised by those skilled in the art without departing from the spirit and scope of the present invention.

What is claimed is:

1. An endoscope connecting system for use in displaying an image from inside a cavity onto a monitor equipment comprising:

a first endoscope comprising a first insertion section insertable into a cavity of an interested object, a control section coupled to said first connection section and an imaging system including first optical illumination means and optical imaging means for transmitting an image of said object so as to be observed through an eyepiece section mounted on said control section;

a second endoscope comprising a second insertion section insertable into a cavity of an interested object, an imaging system including second optical illumination means and a first solid state imaging device for generating a video signal which accepts a visual image information and converts it into an electrical video signal, both said means being incorporated within said second insertion section;

an adaptor detachably mounted on said eyepiece section of said first endoscope, said adaptor including therein a second solid state imaging device which accepts information of said transmitted visual image and converts it into a video signals;

a control unit connectable to said second endoscope and said adaptor, said control unit further comprising an illumination light source for providing light in a red, green and blue sequence and a video signal processor for processing said video signal from said first or second video signal and providing a composite video signal for presenting an image of the object on a monitor equipment.

2. An endoscope connecting system as defined in claim 1, wherein said adaptor has its one end provided with a connector which is incorporated with said second solid state imaging device therein and is detachably mounted on said eyepiece section of said first endoscope and its opposite end provided with a connector adapted to be connected to said video signal processor in said control unit.

3. An endoscope connecting system as defined in claim 2, wherein said illumination light source comprises a light source for emitting illumination light, a regulator for regulating the intensity of light from said light source, filtering means disposed in front of said light source carring color filters of red, green and blue annularly arranged therein at equal angular intervals and a motor for rotating said filtering means.

4. An endoscope connecting system as defined in claim 3, wherein said first and second optical illumination means and said optical image transmission means include optical fiber bundles.

* * * * *